(12) United States Patent
Sandhu et al.

(10) Patent No.: US 8,652,154 B2
(45) Date of Patent: Feb. 18, 2014

(54) NON-RESORBABLE IMPLANTABLE GUIDES

(75) Inventors: Harvinder Sandhu, Scarsdale, NY (US); Maarten Persenaire, Phoenixville, PA (US); James P. Murphy, Newtown Square, PA (US); Charanpreet S. Bagga, Phoenixville, PA (US)

(73) Assignee: Orthovita, Inc., Malvern, PA (US)

( * ) Notice: Subject to any disclaimer, the term of this patent is extended or adjusted under 35 U.S.C. 154(b) by 740 days.

(21) Appl. No.: 11/617,404

(22) Filed: Dec. 28, 2006

(65) Prior Publication Data

US 2008/0161847 A1 Jul. 3, 2008

(51) Int. Cl.
*A61B 17/08* (2006.01)
*A61B 1/32* (2006.01)

(52) U.S. Cl.
USPC .................. 606/151; 600/210; 600/201

(58) Field of Classification Search
USPC .......... 600/201, 206, 212, 222, 229; 606/232, 606/207–208, 151
See application file for complete search history.

(56) References Cited

U.S. PATENT DOCUMENTS

| | | | |
|---|---|---|---|
| 1,054,233 A * | 2/1913 | Lynch | 66/172 R |
| 3,855,638 A | 12/1974 | Pilliar | |
| 4,716,901 A | 1/1988 | Jackson | |
| 4,854,316 A * | 8/1989 | Davis | 606/153 |
| 5,002,572 A * | 3/1991 | Picha | 623/23.74 |
| 5,116,357 A * | 5/1992 | Eberbach | 606/213 |
| 5,147,374 A * | 9/1992 | Fernandez | 606/151 |
| 5,437,672 A | 8/1995 | Alleyne | 606/61 |
| 5,441,508 A * | 8/1995 | Gazielly et al. | 606/151 |
| 5,456,720 A * | 10/1995 | Schultz et al. | 623/23.64 |
| 5,507,811 A * | 4/1996 | Koike et al. | 606/151 |
| 5,593,441 A * | 1/1997 | Lichtenstein et al. | 600/37 |
| 5,611,354 A | 3/1997 | Alleyne | 128/846 |
| 5,686,090 A | 11/1997 | Schilder et al. | 424/423 |
| 5,697,978 A * | 12/1997 | Sgro | 623/23.64 |
| 5,755,769 A * | 5/1998 | Richard et al. | 623/1.2 |

(Continued)

FOREIGN PATENT DOCUMENTS

WO WO-2005/018466 A2 3/2005

OTHER PUBLICATIONS

Eichholz, K.M., et al., "Complications of revision spinal surgery," Neurosurg Focus, 2003, 15(3), 1-4.

(Continued)

*Primary Examiner* — Matthew Lawson
(74) *Attorney, Agent, or Firm* — Stradley Ronon Stevens & Young, LLP (57) ABSTRACT

Surgical devices permitting a surgeon to access repeatedly tissue at a particular surgical site in a patient to perform multiple surgeries over time. The devices have two substantially planar and parallel leaves that are sterile, nonresorbable, and biocompatible. Each leaf forms a continuous structure and defines the entire longitudinal length of the device to accommodate the size and location of the surgical site. A base member is located in situ and adjacent the surgical site. An anchoring surface secures the device to the tissue of the patient at the surgical site. The leaves have a conjoined portion such that a manual force is required to separate the leaves, thereby expeditiously creating a pathway through which access to the tissue at the surgical site is realized with minimal tissue dissection, and the proximal ends of the leaves are not conjoined to facilitate separation of the leaves and creation of the pathway.

22 Claims, 10 Drawing Sheets

(56) References Cited

U.S. PATENT DOCUMENTS

| | | | |
|---|---|---|---|
| 5,813,975 A * | 9/1998 | Valenti | 600/37 |
| 5,868,745 A | 2/1999 | Alleyne | 606/61 |
| 6,031,148 A | 2/2000 | Hayes et al. | 623/11 |
| 6,033,426 A | 3/2000 | Kaji | |
| 6,093,205 A * | 7/2000 | McLeod et al. | 623/17.16 |
| 6,113,623 A * | 9/2000 | Sgro | 606/215 |
| 6,120,539 A * | 9/2000 | Eldridge et al. | 623/11.11 |
| 6,371,968 B1 | 4/2002 | Kogasaka et al. | |
| 6,383,201 B1 * | 5/2002 | Dong | 606/151 |
| 6,454,767 B2 | 9/2002 | Alleyne | 606/61 |
| 6,592,515 B2 * | 7/2003 | Thierfelder et al. | 600/37 |
| 6,652,595 B1 * | 11/2003 | Nicolo | 623/23.74 |
| 6,736,823 B2 | 5/2004 | Darois et al. | 606/151 |
| 6,736,854 B2 | 5/2004 | Vadurro et al. | 623/23.72 |
| 6,790,213 B2 | 9/2004 | Cherok et al. | 606/151 |
| 6,814,700 B1 * | 11/2004 | Mueller et al. | 600/206 |
| 6,926,723 B1 | 8/2005 | Mulhauser et al. | 606/151 |
| 6,966,916 B2 | 11/2005 | Kumar | 606/144 |
| 7,081,135 B2 * | 7/2006 | Smith et al. | 623/8 |
| 7,101,381 B2 * | 9/2006 | Ford et al. | 606/151 |
| 7,144,368 B2 * | 12/2006 | Larson et al. | 600/215 |
| 7,407,483 B2 * | 8/2008 | Perez-Cruet et al. | 600/219 |
| 7,413,569 B2 * | 8/2008 | Sogaard-Andersen | 606/151 |
| 7,828,854 B2 * | 11/2010 | Rousseau et al. | 623/23.72 |
| 2002/0137989 A1 * | 9/2002 | Clem et al. | 600/210 |
| 2004/0087980 A1 * | 5/2004 | Ford et al. | 606/151 |
| 2004/0209538 A1 * | 10/2004 | Klinge et al. | 442/59 |
| 2005/0021058 A1 * | 1/2005 | Negro | 606/151 |
| 2005/0043818 A1 * | 2/2005 | Bellon Caneiro et al. | 623/23.72 |
| 2005/0080317 A1 * | 4/2005 | Merade | 600/30 |
| 2005/0177155 A1 * | 8/2005 | Alleyne | 606/61 |
| 2005/0261782 A1 | 11/2005 | Hoganson | |
| 2005/0273120 A1 | 12/2005 | Abdou | 606/151 |
| 2006/0155170 A1 * | 7/2006 | Hanson et al. | 600/201 |
| 2006/0178683 A1 * | 8/2006 | Shimoji et al. | 606/151 |
| 2006/0282105 A1 * | 12/2006 | Ford et al. | 606/151 |
| 2007/0225568 A1 * | 9/2007 | Colleran | 600/201 |
| 2008/0242940 A1 * | 10/2008 | Stefanchik | 600/235 |
| 2010/0057114 A1 * | 3/2010 | Butler | 606/151 |

OTHER PUBLICATIONS

Fritsch E.W., et al., "The failed back surgery syndrome; reasons intraoperative findings, and long-term results: A report of 182 operative treatments," Spine, 1996, 21(5), 626-633.

Malter, A.D., et al., "5-year reoperation rates after different types of lumbar spine surgery," Spine, 1998, 23(7), 814-820.

McKinley, D., et al., "Cost effectiveness evaluation of ADCON®-L adhesion control gel in lumbar surgery," Neurol. Res., 1999, vol. 21, Suppl. 1, S67-S71.

Zheng, F., et al., "Factors predicting hospital stay, operative time, blood loss, and transfusion in patients undergoing revision posterior lumbar spine decompression, fusion, and segmental instrumentation," Spine, 2002, 27(8), 818-824.

International Search Report from International Application No. PCT/US2007/024739 issued by the European Patent Office on Apr. 8, 2008.

International Preliminary Report on Patentability with Written Opinion of the ISA (EPO) for International Application No. PCT/US07/24739 issued by the IB of WIPO on Jun. 30, 2009.

Examiner's First Report on Patent Application No. 2007339354 issued by the Australian Intellectual Property Office on May 23, 2012.

Official Action from the Israel Patent Office dated Apr. 17, 2012.

* cited by examiner

NON-RESORBABLE IMPLANTABLE GUIDES

FIELD OF THE INVENTION

The invention described herein relates to devices, and methods of their use, for facilitating access to a surgical situs.

BACKGROUND OF THE INVENTION

Many surgical patients will return for additional surgery. This is particularly acute in orthopedics, especially spine surgery. ((a) Fritsch E., Heisel J., et al. *Spine* 1996 Mar. 1; 21(5):626-33. (b) Malter A., McNeney B., et al. *Spine* 1998 Apr. 1; 23(7): 814-20. (c) Zheng F., Cammisa F., et al. *Spine* 2002; 27(8): 818-24.)

Secondary surgeries are challenging because bony landmarks have often been removed (as with a laminectomy) and dense adherent scar tissue may have formed that needs to be removed from underlying structures. The subsequent surgery can take significantly longer (60 minutes or more) as the surgeon carefully removes any dense adherent tissues and slowly finds his way with aid of the remaining anatomical landmarks. See, e.g., McKinley D., Shaffer L. *Neurol Res.* 1999; 21 Suppl 1:S67-71. Challenging surgeries can put the patient at additional risk, increasing the chance of complications such as infection, spinal cord or nerve root damage, and dural tears. (Eichholz K., Ryken T., *Neurosurg. Focus* 2003 Sep 15: 15(3); E1.).

The surgery market is in need of a system that helps the surgeon manage any dense adherent tissue formation and facilitate the surgical navigation to quickly obtain the appropriate surgical exposure while protecting delicate tissues, such as, for example, the dura and nerve roots.

SUMMARY OF THE INVENTION

The present invention relates to nonresorbable, biocompatible, sterile surgical access devices comprising first and second, substantially planar, leaves, each having first and second surfaces; the first surfaces of the leaves being conjoined along at least a portion of their peripheries, such that the leaves can be separated from each other to define an access space between the first and second leaves. The present invention also relates to nonresorbable, biocompatible, sterile surgical access devices comprising a base member and at least one hollow projection pendant to the base member. Additionally, the invention provides for methods of using these devices for facilitating access to a site where revision surgery or multiple surgeries are to be performed and methods of accessing a site where revision surgery or multiple surgeries are to be performed.

BRIEF DESCRIPTION OF THE DRAWINGS

FIGS. 7A, 7B, and 7C depict exemplary contact patterns of the leaves of the present invention. As shown in FIG. 7A, the leaves are intermittently conjoined so as to form a pattern of squares. As shown in FIG. 7B, the leaves are intermittently conjoined so as to form a pattern of rectangles. As shown in FIG. 7C, the leaves are intermittently conjoined so as to form a pattern of diamonds.

DETAILED DESCRIPTION OF ILLUSTRATIVE EMBODIMENTS

The present invention provides for devices for facilitating access to a site where surgery is to be performed, as well as methods for their use. Once placed within a surgical situs, the present invention may be located and accessed at a later time. Once accessed, the devices of the present invention are used to expeditiously create a space or pathway through which access to a surgical situs may be realized, with minimal tissue dissection.

These sterile devices can be employed whenever there exists a likelihood of additional surgery at a surgical situs. Such situations include, but are not limited to, posterior and anterior spinal surgery such as laminectomy and intercorporeal fusion, pacemaker implantation, and joint replacement. The devices of the present invention may be fabricated to accommodate the size and location of a particular surgical situs.

In addition to facilitating access to a surgical situs, the devices described herein may protect the situs from the infiltration of scar tissue. Such protection would provide a reduction in the incidence of subsequent surgery that would be necessitated by such infiltration.

As shown in FIGS. 1-8, an access device 1 comprises first (5) and second (6) leaves, each having first and second surfaces. In preferred embodiments, these leaves are substantially planar. In certain iterations of the present invention, the leaves form a continuous structure. Examples of such iterations are shown in FIGS. 1B-1C.

The device may be comprised of sterilizable films or polymer fabrics such as, but not limited to, polyether ether ketone, polypropylene, polyethylene, polyester, polytetrafluoroethylene, and carboxymethylcellulose. In certain embodiments, the leaves comprise generally rigid material. In preferred embodiments, the leaves comprise generally flexible or pliable material so as to conform to the shape of surrounding anatomical structures within the surgical situs. In some embodiments, the leaves are generally non-porous or have an engineered porosity to allow incorporation of the device in the body without dense adherent tissue. In other embodiments, the leaves comprise pore sizes less than about one micron. In other embodiments, pore sizes may be about 10 microns to about 1000 microns. In certain embodiments, the first surface of each leaf may have one porosity and the second surface of each leaf may have a second porosity. In some instances, the surfaces of the leaves may comprise porosity gradients wherein each surface may, independently, contemporaneously comprise areas of higher porosity and areas of lesser porosity. In other instances, each leaf may be a two or multiple-ply structure with each ply having a certain porosity or non-porosity.

According to the present invention, the first surfaces of the leaves are conjoined along at least a portion of their peripheries. In some embodiments, the leaves are conjoined substantially along the first surfaces of the leaves (FIGS. 1A-1C, 6). In others, the leaves are conjoined intermittently along the length of the leaves. Such intermittent contact may be such so as to form patterns of contact between the leaves (FIGS. 7A-7C, 8A-8B). Two leaves may be conjoined using various methods, including, for example, staples, stitches or sutures, biocompatible glue, ultrasonic welding, interweaving, overmolding, or heat sealing. Alternatively, two leaves may be conjoined via the use of one or more additional materials, wherein the first surface of at least one leaf is fastened to the additional material using methods including, for example, staples, stitches or sutures, biocompatible glue, ultrasonic welding, interweaving, overmolding, or heat sealing. The first surfaces of the leaves are preferably conjoined such that the leaves can be separated from each other to define an access space between the leaves. Those skilled in the art will be able to conjoin the leaves such that varying amounts of force are required to separate the leaves. For example, the leaves may be conjoined such that a manual force of between about 1 and 4 pounds per linear inch is required to separate the leaves. The leaves may also be conjoined such that greater forces are required to separate the leaves.

Figure 1A:
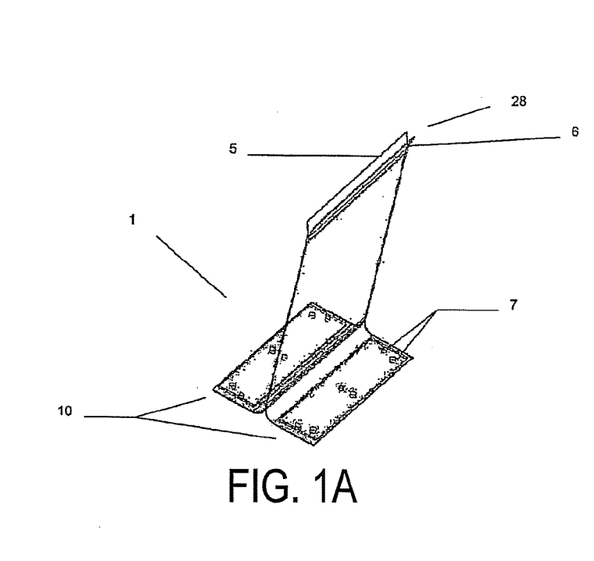
FIG. 1A depicts one embodiment of the present invention comprising leaves that are separable from each other so as to define a space between the leaves.

In one embodiment, shown for example in FIG. 1A, the first surfaces of the proximal ends (28) of the first and second leaves are not in contact with each other. Such a configuration could be desirable so as to facilitate the separation of the leaves from each other so as to define a space between the leaves.

Figure 1B:
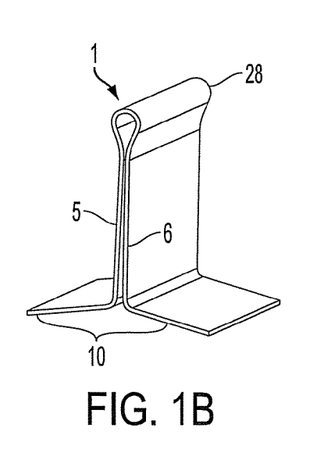
FIG. 1B depicts another embodiment of the present invention wherein the leaves form a continuous structure.
Figure 1C:
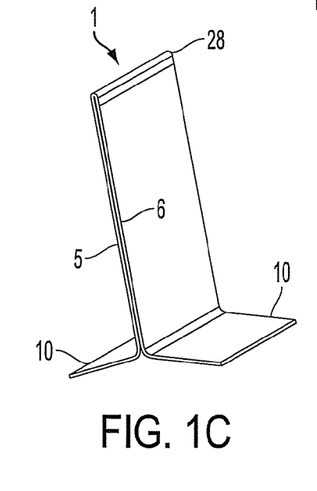
FIG. 1C depicts another embodiment of the present invention wherein the leaves form a continuous structure.
Figure 8A:
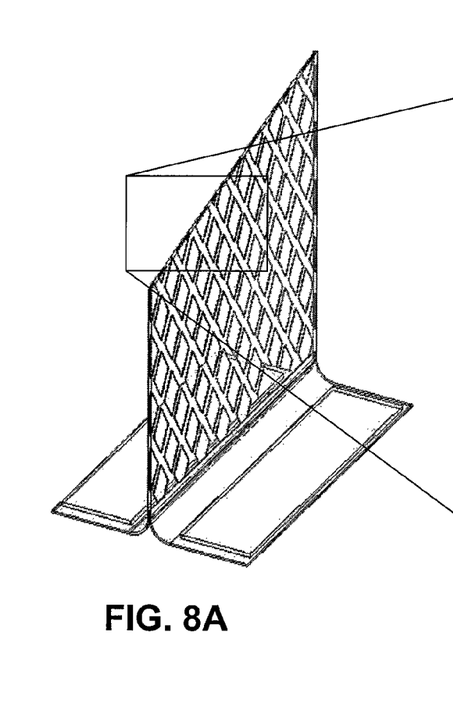
FIG. 8A depicts one embodiment of the present invention wherein the proximal end of the device has been cut and removed.
Figure 8B:
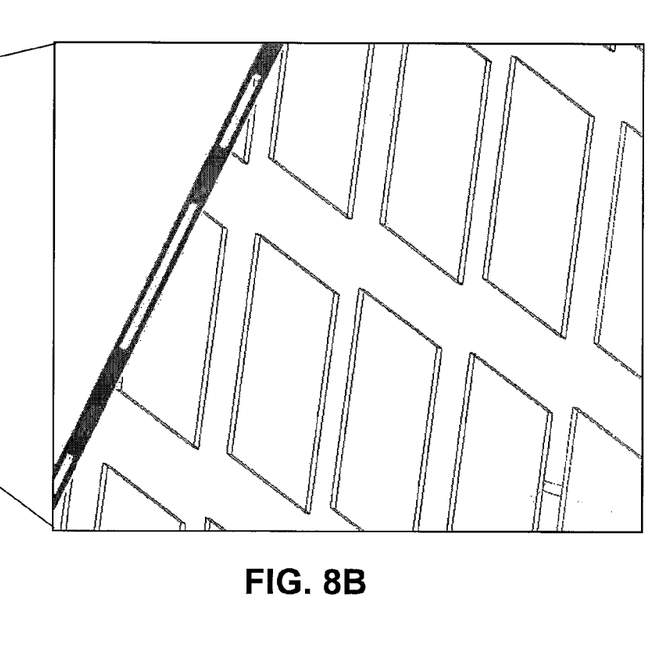
FIG. 8B is an expanded view of the resulting cut edge, depicting the spaces between the leaves that have been revealed by the cutting of the proximal end.

In those embodiments wherein the leaves form a continuous structure, for example, such as those shown in FIGS. 1B-1C, the proximal end (28) of the device may be cut using surgical cutting instruments to facilitate the separation of the leaves. In those embodiments wherein the leaves are conjoined intermittently along their lengths, the proximal end of the device may also be cut with surgical cutting instruments to expose those areas wherein the leaves are not in contact with each other, as shown in FIGS. 8A-8B. Such exposure may facilitate the separation of the leaves.

In certain embodiments, the leaves may be joined by further biocompatible material. In such embodiments, when the leaves are separated from each other, a generally hollow structure is formed. This generally hollow structure may also be collapsible.

It may be desirable that the surfaces of the devices of the present invention are textured. Such texturing may be useful in providing tactile guidance and may improve the positioning of the device within the surgical situs.

In preferred iterations, it may be desirable for the present invention to comprise a base member for placement and affixation of the device within a surgical situs. In some embodiments, for example those shown in FIGS. 1A-1C, the distal end of at least one of the leaves of the present invention may form a base member 10. In other embodiments, the base member is formed from the distal end of each of the leaves. In such embodiments, the opposing faces of the distal ends of the leaves are not in contact with each other and may be freely movable. For example, the distal ends may be movable such that they may be oriented generally normal to the proximal ends of the leaves.

Figure 6:
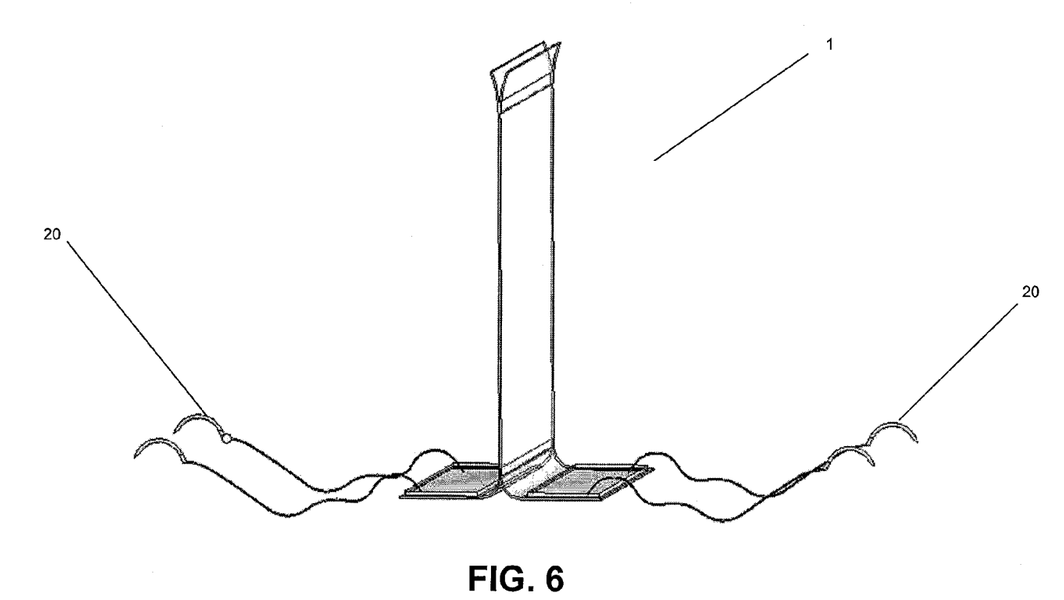
FIG. 6 depicts an embodiment of the present invention comprising sutures.
Figure 7A:
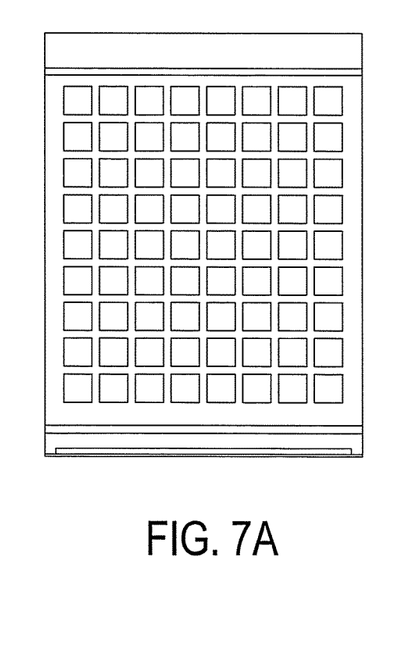
Figure 7B:
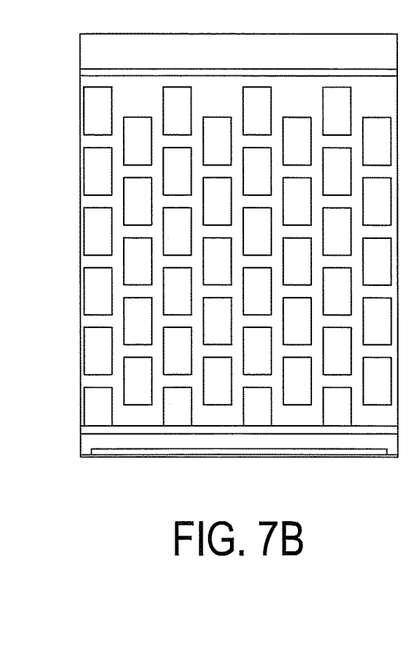
Figure 7C:
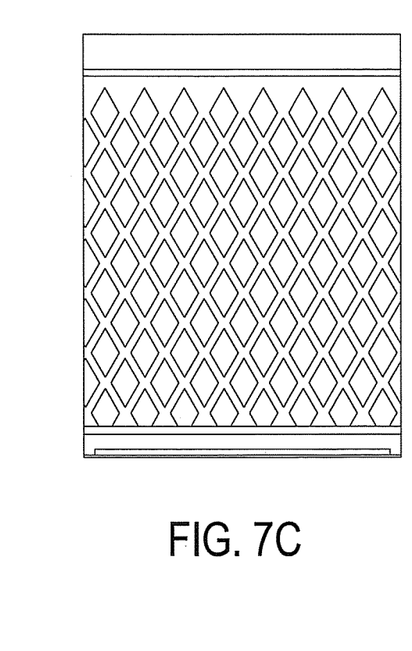

The leaves of the present invention further comprise at least one anchoring surface. As used herein, "anchoring" is contemplated to include all modes of securing the device within a surgical situs. For example, such modes include, but are not limited to, suturing and the use of biocompatible glue. Anchoring is also contemplated to occur through the natural growth of tissue onto or surrounding the adhering surface or through natural friction or pressure exerted on the device from surrounding tissues. In preferred embodiments, an anchoring surface is located on the distal end of at least one of the leaves. In other preferred embodiments, an anchoring surface is located on the proximal end of at least one of the leaves. The anchoring surfaces may further comprise attachment surfaces to facilitate the anchoring of the device to tissue. The anchoring surface may further comprise apertures 7 (See FIG. 1A). The apertures may be used for attachment of the distal ends to tissue. As seen in FIG. 6, for example, in certain embodiments, the anchoring surface may further comprise sutures 20.

In certain embodiments, the leaves are pendant to a biocompatible base member. In some embodiments, the leaves are oriented generally normal to the base member. In others, the leaves extend generally upward from the base member. The base member may comprise at least one anchoring surface. The anchoring surfaces may further comprise attachment surfaces to facilitate the anchoring of the device to tissue. In some embodiments, the anchoring surfaces may comprise apertures. The apertures may be used for attachment of the anchoring surfaces to tissue. In certain embodiments, the anchoring surface of the base member may further comprise sutures.

Figure 2A:
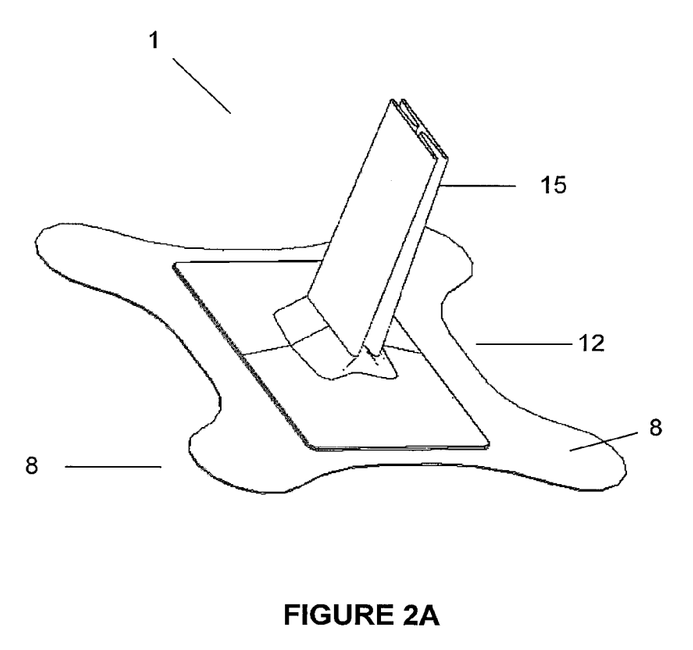
FIG. 2A depicts one embodiment of the present invention comprising a base member and at least one hollow projection, wherein the hollow projection is collapsed so as to minimize the area within the hollow projection.
Figure 2B:
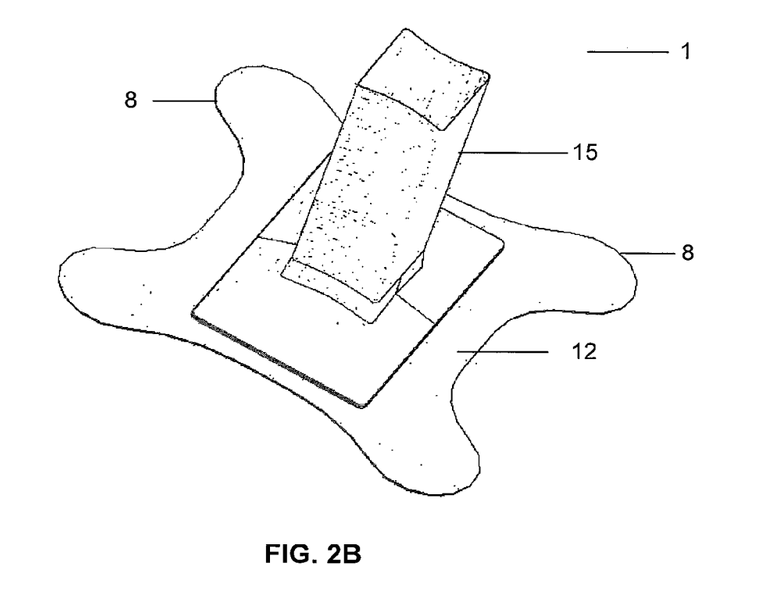
FIG. 2B depicts one embodiment of the present invention comprising a base member and at least one hollow projection, wherein the hollow projection is expanded so as to maximize the area within the hollow projection.
Figure 2C:
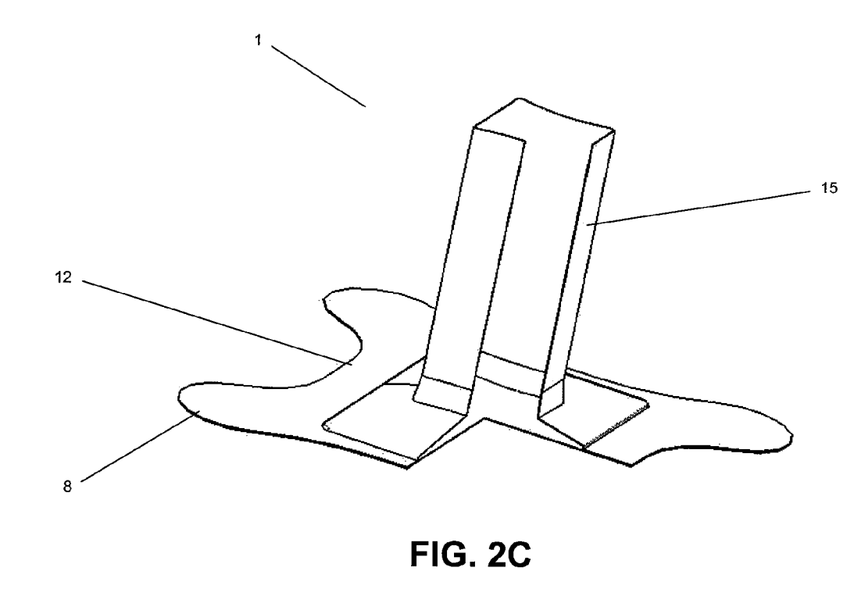
FIG. 2C depicts one embodiment of the present invention detailing a cut-away view of the hollow projection.
Figure 3:
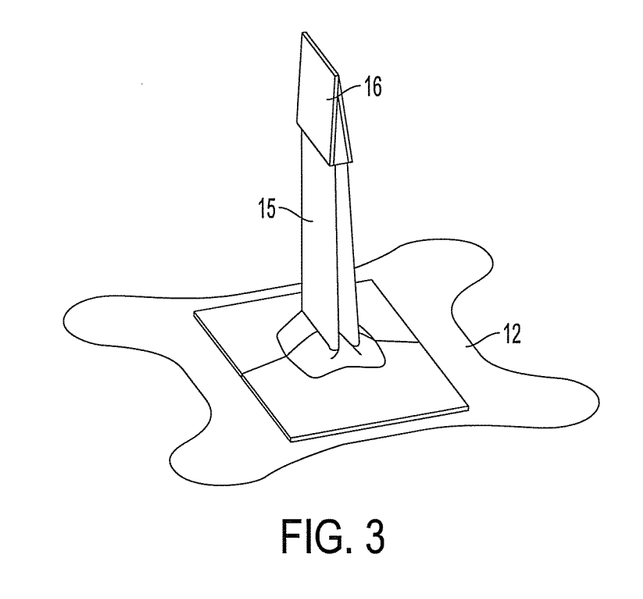
FIG. 3 depicts one embodiment of the present invention comprising an enclosing member.
Figure 4:
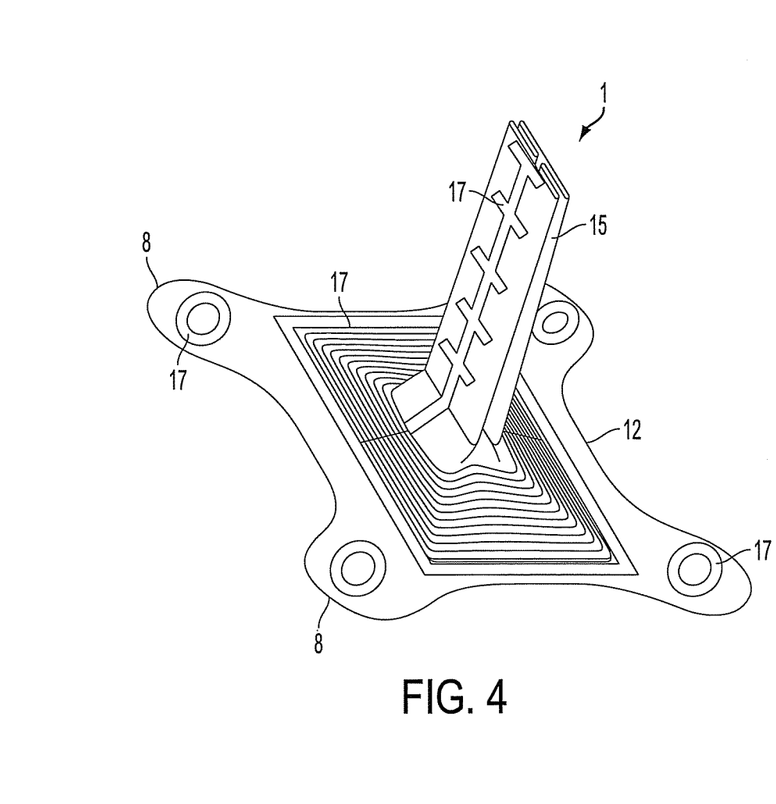
FIG. 4 depicts one embodiment of the present invention comprising radiographic markers.

Another embodiment of the present invention is shown in FIGS. 2-4, comprising an access device comprising a biocompatible base member (12) and at least one hollow projection (15) pendant to the base member. The hollow projection may be oriented in a direction that is generally normal to the base member. In some variants, the hollow projection extends generally upward from the base member. In certain embodiments, the hollow projection is collapsible, wherein the area of the open space within the hollow projection is minimized, as depicted in FIG. 2A. The hollow projection may also be expandable, wherein the area of the open space within the hollow projection is maximized, as shown in FIG. 2B. The cross-section of the hollow projection may be generally circular, oval, rectangular, or square. A cut-away view of one embodiment of the present invention is shown in FIG. 2C.

In certain embodiments, the hollow projection may further comprise at least one anchoring surface. The anchoring surfaces may further comprise attachment surfaces to facilitate the anchoring of the device to tissue. In some embodiments, the anchoring surfaces may comprise apertures. The apertures may be used for attachment of the anchoring surfaces to tissue. In certain embodiments, the anchoring surface of the hollow projection may further comprise sutures.

The base member may also further comprise at least one anchoring surface. The anchoring surfaces may further comprise attachment surfaces (8) to facilitate the anchoring of the device to tissue. In some embodiments, the anchoring surfaces may comprise apertures. The apertures may be used for attachment of the anchoring surfaces to tissue. In certain embodiments, the anchoring surface of the base member may further comprise sutures.

In some embodiments, for example as shown in FIG. 3, the hollow projection further comprises an enclosing member 16 at the proximal end of the access device. The enclosing member can, for example, guard against the infiltration of materials into the space within the hollow projection, maintaining the sterility of the space. In certain embodiments, the enclosing member may be integral to the hollow projection such that it may be cut using surgical cutting instruments to expose the area within the hollow projection. In other embodiments, the enclosing member may be comprised of biocompatible material that is expandable, wherein it may be opened so as to expose the area within the hollow projection. The enclosing member may further comprise radiographic or radiopaque marker materials such as stainless steel, nitinol, barium glass, or barium sulfate impregnated polymers.

The enclosing member may further comprise at least one anchoring surface. The anchoring surfaces may further comprise attachment surfaces to facilitate the anchoring of the device to tissue. In some embodiments, the anchoring surfaces may comprise apertures. The apertures may be used for attachment of the anchoring surfaces to tissue using, for example, sutures.

Figure 5A:
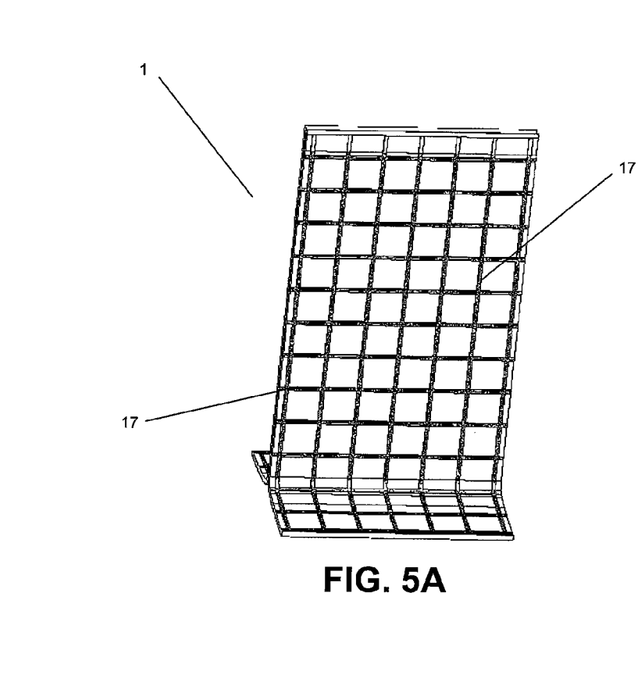
FIG. 5A depicts another embodiment of the present invention comprising radiographic markers.
Figure 5B:
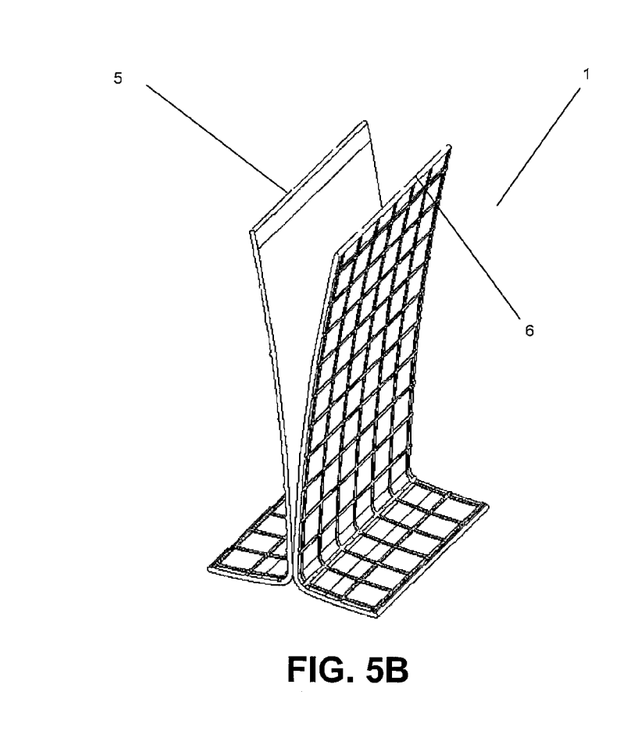
FIG. 5B depicts another view of an embodiment of the present invention comprising radiographic markers wherein the leaves are being separated.

Devices of the present invention may further comprise at least one locating region. The locating regions may comprise materials to facilitate the identification and location of the device within a surgical situs. Such materials may include radiographic or radiopaque marker materials. Radiographic or radiopaque marker materials include, but are not limited to, stainless steel, nitinol, barium glass, or barium sulfate impregnated polymers. The marker materials may be positioned anywhere on the devices or within the structure of the devices. For example, the marker materials may be positioned anywhere on, or within, at least one of the leaves. In other examples, the marker materials may be positioned anywhere on, or within, the hollow projection. In those embodiments comprising a base member, the marker materials may also be positioned anywhere on the base material. These marker materials may be used to define the depth of the device, areas of interest on the device such as the perimeter of the base member, the distal ends of the device, or particular design features of the device. The material may also be used to assist in the identification of anatomical features within the surgical situs. FIG. 4 depicts one embodiment of the present invention wherein radiopaque material 17 has been incorporated into the device of the present invention. FIGS. 5A and 5B depict another embodiment of the present invention comprising radiopaque material 17.

Devices of the present invention may also comprise energy-emitting materials, for example, materials that emit vibrational or thermal energy or radio frequencies. Such energies could be used in patient therapy or for locating the device within the situs.

It is also within the scope of the present invention that the devices described herein further comprise visual markers, for example, colored polymers. These markers may be used as localizing markings so that the depth and location of the device within the surgical situs may be determined. In some embodiments, the device may be colored so as to be a color that contrasts with the color of bodily tissues, for example bone and blood, so as to facilitate the locating of the device within a surgical situs. Such colors include, but are not limited to, orange, blue, purple and green.

In some instances, it may be desired to administer fluids or medicaments to the surgical situs. As such, it may be desirable that the devices of the present invention further comprise catheters or cannulas. The catheters or cannulas may be positioned along the longitudinal axis of the device such that the distal end of the catheter or cannula is positioned at, or in close proximity to, the surgical situs. After the device is placed within the surgical situs, fluids or medicaments may be delivered to the surgical situs by introduction through the externally communicating proximate end of the catheter or cannula.

In accordance with the present invention, to facilitate access to a site where surgery is to be performed, a device as described herein comprising first and second, substantially planar, leaves, each having first and second surfaces; the first surfaces of the leaves being conjoined along at least a portion of their peripheries, such that the leaves can be separated from each other to define an access space between the first and second leaves, is placed within the situs of the surgery at a location where subsequent surgical access may be required. The leaves are then affixed to tissue within the situs. Affixation may be achieved using a variety of methods, including, but not limited to, suturing or biocompatible glue. It is also envisioned that affixation may occur through the natural growth of tissue surrounding the device or through natural friction or pressure exerted on the device from surrounding tissues.

To access a site where subsequent surgery is to be performed, one locates the device of the present invention. Location may be accomplished in several ways. In some embodiments, the device may comprise radiographic or radiopaque material markers. In such embodiments, the device may be located using X-ray or other radiographic or imaging technique known in the art. In those embodiments where the device comprises materials that emit energy, the device may be located using techniques known in the art. After the device has been located, it can be accessed through an incision at the site of the device. Once the device is accessed, the leaves of the device may be separated so as to define a space between the leaves. The resulting space provides a pathway to the surgical situs. In may be convenient for a retractor to be used to maintain the space between the leaves.

Also within the scope of the invention are methods for facilitating access to a site where surgery is to be performed comprising placing within the situs of the surgery at a location where subsequent surgical access may be required, a device comprising a biocompatible base member and at least one hollow projection pendant to the base member. Once the device is placed within the situs, the base member and/or the hollow projection is affixed to tissue within the situs. Fixation may be achieved using a variety of methods, including, but not limited to, suturing or biocompatible glue. It is also envisioned that affixation may occur through the natural growth of tissue surrounding the device or through natural friction or pressure exerted on the device from surrounding tissues.

To access a site where surgery is to be performed, one locates the device of the present invention using techniques as described herein. After the device has been located, it can be accessed through an incision at the site of the device. Once the device is accessed, the hollow space within the hollow projection may be exposed. The resulting space provides a pathway to the surgical situs. In may be convenient for a retractor to be used to maintain the space between the leaves. In those embodiments wherein the device comprises an enclosing member, the space within the hollow projection may be accessed by cutting away the enclosing member. Alternatively, the space may be exposed by expanding the enclosing member to reveal the space within the hollow projection or collapsed leaves.

While certain embodiments of the present invention have been described herein, it will be apparent to those of skill in the art that these embodiments are exemplary rather than limiting.

What is claimed:

1. A surgical access device having a longitudinal axis and permitting a surgeon to access repeatedly tissue at a particular surgical site in a patient to perform multiple surgeries over time, the device comprising:

first and second substantially planar leaves that are sterile, nonresorbable, and biocompatible, each leaf forming a continuous structure between distal and proximal ends along a longitudinal length, each leaf lying in parallel along the longitudinal axis of the device, each leaf defining the entire longitudinal length of the device to accommodate the size and location of the particular surgical site, and each leaf having areas of higher porosity and areas of lesser porosity, wherein the distal ends of the leaves are freely movable;

a base member formed from at least one of, or as a separate structure secured to at least one of, the distal ends of the planar leaves, the base member adapted to be located in situ and adjacent the surgical site; and an anchoring surface located on at least one of the leaves or on the base member, the anchoring surface securing the device to the tissue of the patient at the surgical site;

the leaves being conjoined along the longitudinal length of the leaves to form a conjoined portion such that a manual force is required to separate the leaves, thereby expeditiously creating a space or pathway through which access to the tissue at the surgical site is realized with minimal tissue dissection, and the proximal ends of the leaves are not conjoined to facilitate separation of the leaves and creation of the space or pathway.

2. The device of claim 1 wherein at least one leaf further comprises at least one anchoring surface.

3. The device of claim 2 wherein the anchoring surface further comprises at least one suture.

4. The device of claim 1 wherein at least a portion of the device is radiopaque.

5. The device of claim 1 further comprising localizing markings.

6. The device of claim 1 further comprising a catheter or cannula.

7. The device of claim 1 wherein the device is a contrasting color to tissue.

8. The device of claim 1, wherein the distal ends of the leaves have higher porosity and the conjoined portion has lesser porosity.

9. The device of claim 1, wherein the distal ends of the leaves are freely movable such that they may be oriented generally normal to the proximal ends of the leaves.

10. The device of claim 1, wherein the manual force is between 1 and 4 pounds per linear inch.

11. The device of claim 1, wherein the leaves are flexible.

12. A surgical access device having a longitudinal axis and permitting a surgeon to access repeatedly tissue at a particular surgical site in a patient to perform multiple surgeries over time, the device comprising:

first and second substantially planar leaves that are sterile, nonresorbable, and biocompatible, each leaf forming a continuous structure between distal and proximal ends along a longitudinal length, each leaf lying in parallel along the longitudinal axis of the device, and each leaf defining the entire longitudinal length of the device to accommodate the size and location of the particular surgical site, wherein the distal ends of the leaves are freely movable;

a base member formed from at least one of or as a separate structure secured to at least one of, the distal ends of the planar leaves, the base member adapted to be located in situ and adjacent the surgical site; and an anchoring surface located on at least one of the leaves or on the base member, the anchoring surface securing the device to the tissue of the patient at the surgical site;

the leaves being conjoined along the longitudinal length of the leaves to form a conjoined portion such that a manual force is required to separate the leaves, thereby expeditiously creating a space or pathway through which access to the tissue at the surgical site is realized with minimal tissue dissection, and the proximal ends of the leaves are not conjoined to facilitate separation of the leaves and creation of the space or pathway.

13. The device of claim 12, wherein the distal end of each leaf has higher porosity and the conjoined portion has lesser porosity.

14. The device of claim 12, wherein the distal ends of the leaves are freely movable such that they may be oriented generally normal to the proximal ends of the leaves.

15. The device of claim 12, wherein the manual force is between 1 and 4 pounds per linear inch.

16. The device of claim 12, wherein the leaves are flexible.

17. The device of claim 12 wherein at least one leaf further comprises at least one anchoring surface.

18. The device of claim 17 wherein the anchoring surface further comprises at least one suture.

19. The device of claim 12 wherein at least a portion of the device is radiopaque.

20. The device of claim 12 further comprising localizing markings.

21. The device of claim 12 further comprising a catheter or cannula.

22. The device of claim 12 wherein the device is a contrasting color to tissue.

* * * * *